(12) United States Patent
Nakajima (10) Patent No.: US 7,256,892 B2
(45) Date of Patent: Aug. 14, 2007

(54) MEASURING INSTRUMENT AND FLUOROMETRIC METHOD

(75) Inventor: Shinya Nakajima, Kyoto (JP)

(73) Assignee: Arkray, Inc., Kyoto (JP)

( * ) Notice: Subject to any disclaimer, the term of this patent is extended or adjusted under 35 U.S.C. 154(b) by 138 days.

(21) Appl. No.: 10/534,182

(22) PCT Filed: Nov. 13, 2003

(86) PCT No.: PCT/JP03/14421

§ 371 (c)(1),
(2), (4) Date: May 6, 2005

(87) PCT Pub. No.: WO2004/044564

PCT Pub. Date: May 27, 2004

(65) Prior Publication Data

US 2006/0108540 A1    May 25, 2006

(30) Foreign Application Priority Data

Nov. 14, 2002 (JP) ............................. 2002-330787

(51) Int. Cl.
  G01N 21/25 (2006.01)
  F21V 9/16 (2006.01)
  B32B 5/02 (2006.01)
(52) U.S. Cl. .................. 356/417; 250/458.1; 422/82.08
(58) Field of Classification Search ................. 356/417; 250/458.1; 422/82.08
See application file for complete search history.

(56) References Cited

U.S. PATENT DOCUMENTS 6,466,316 B2 * 10/2002 Modlin et al. ............... 356/318

2002/0090630 A1 * 7/2002 Hazama ........................ 435/6

FOREIGN PATENT DOCUMENTS

| JP | 5-72039 | 3/1993 |
|---|---|---|
| JP | 9-21749 | 1/1997 |
| JP | 2000-503774 | 3/2000 |
| JP | 2002-168868 | 6/2002 |
| JP | 2003-83894 | 3/2003 |
| WO | WO 97/46963 | 11/1997 |

* cited by examiner

Primary Examiner—Roy M. Punnoose
(74) Attorney, Agent, or Firm—Hamre, Schumann, Mueller & Larson, P.C.

(57) ABSTRACT

A measuring instrument that comprises a light source unit 1 capable of emitting light having different wavelengths, a light receiving unit 2 that outputs an electrical signal corresponding to an intensity of transmitted light or radiated light from a sample 6 mixed with a plurality of coloring matters, and a calculation section 3, is used. The calculation section 3 uses a previously calculated correction coefficient to calculate the fluorescence intensity of transmitted light or radiated light for each coloring matter. The correction coefficient is calculated based on an electrical signal output by the light receiving unit 2 when a plurality of correction samples are irradiated with light having different wavelengths, each correction sample being mixed with any one of the coloring matters and the respective mixed coloring matters being different from one another.

3 Claims, 4 Drawing Sheets

MEASURING INSTRUMENT AND FLUOROMETRIC METHOD

TECHNICAL FIELD

The present invention relates to a measuring instrument for measuring an intensity of transmitted light or radiated light for each coloring matter when a sample mixed with a plurality of coloring matters is irradiated with light having wavelengths corresponding to the respective coloring matters. More particularly, the present invention relates to a fluorescence measuring instrument and a fluorometric method of irradiating a sample mixed with a plurality of fluorescent coloring matters, with light having excitation wavelengths of the fluorescent coloring matters, to measure fluorescence excited by the light.

BACKGROUND ART

In recent years, analysis of various components, genetic diagnosis and the like are performed by measurement of fluorescence, absorbance or reflectance. For example, in component analysis using fluorescence measurement, a sample mixed with a coloring matter (fluorescent coloring matter) is irradiated with light, and an intensity of fluorescence excited by the light is measured to detect a material labeled with the coloring matter (fluorescent coloring matter).

In component analysis using absorbance measurement, a sample mixed with a coloring matter is irradiated with light having a wavelength corresponding to the coloring matter, and an intensity of transmitted light is measured to calculate absorbance, thereby detecting a material labeled with the coloring matter, as disclosed in, for example, JP No. 9-21749A. In component analysis using reflectance measurement, an intensity of scattered light, instead of transmitted light, is measured to calculate reflectance, thereby detecting a material labeled with the coloring matter.

In the case of detection of a plurality of materials using the above-described component analysis, a sample is mixed with a plurality of different coloring matters that vary depending on the materials to be detected, and the sample is irradiated with light corresponding to each coloring matter separately.

In the case of fluorescence measurement, component analysis is performed by irradiating a sample mixed with a plurality of coloring matters (fluorescent coloring matters) that have different excitation wavelengths and fluorescence wavelengths, with light having the excitation wavelength of each coloring matter separately, and measuring a fluorescence intensity of the coloring matter, as disclosed in, for example, JP 2000-503774A.

In the case of absorbance measurement, component analysis is performed by irradiating a sample mixed with a plurality of coloring matters having different absorption wavelengths, with light having the absorption wavelength of each coloring matter separately, to measure an intensity of transmitted light for each coloring matter.

However, in general, the excitation wavelength, absorption wavelength and reflection wavelength of a coloring matter have a certain width. Therefore, in fluorescence measurement, if the coloring matters (fluorescent coloring matters) used have close excitation peak wavelengths, when a certain coloring matter is excited by light with its excitation wavelength, other coloring matter(s) also may be excited by the light. In this case, the resultant fluorescence intensity is a value obtained by combining the fluorescence intensity of each excited coloring matter, thereby making it difficult to perform accurate component analysis, genetic diagnosis or the like.

The same is true of absorbance measurement and reflectance measurement. Specifically, the resultant intensity of transmitted light or scattered light is a value obtained by combining the intensity of transmitted light or scattered light for each coloring matter, thereby making it difficult to perform accurate component analysis, genetic diagnosis or the like.

An object of the present invention is to provide a measuring instrument and a fluorometric method capable of separating and measuring an actual intensity of each coloring matter from a combined value of the intensity of transmitted light or radiated light.

DISCLOSURE OF INVENTION

To achieve the above-described object, a measuring instrument of the present invention is a measuring instrument for measuring an intensity of transmitted light or radiated light for each coloring matter when a sample mixed with a plurality of coloring matters is irradiated with light having different wavelengths. The measuring instrument comprises a light source unit capable of irradiating the sample with the light having the different wavelengths; a light receiving unit that receives the transmitted light or the radiated light and outputs an electrical signal corresponding to the intensity of the received light; and a calculation section. The calculation section calculates the intensity of the transmitted light or the radiated light for each of the coloring matters using a correction coefficient that is calculated based on an electrical signal output by the light receiving unit when the light source unit irradiates each of a plurality of correction samples with light having a different wavelength from each other, each correction sample being mixed with one of the plurality of coloring matters and the mixed coloring matters being different from one another.

In the measuring instrument of the present invention, the sample may be mixed with a plurality of fluorescent coloring matters having different excitation wavelengths as the coloring matters. The light receiving unit may receive fluorescence of the fluorescent coloring matters, and output an electrical signal corresponding to a fluorescence intensity of the received fluorescence. The calculation section may calculate the fluorescence intensity of the fluorescence of each of the fluorescent coloring matters emitted from the sample using a correction coefficient that is calculated based on an electrical signal output by the light receiving unit when the light source unit irradiates each of a plurality of correction samples, each correction sample being mixed with one of the plurality of fluorescent coloring matters and the respective mixed fluorescent coloring matters being different from one another, with light having a corresponding excitation wavelength of the plurality of fluorescent coloring matters. In this embodiment, the measuring instrument of the present invention functions as a fluorometric device.

In the embodiment in which the measuring instrument functions as a fluorescence measuring instrument, preferably, the correction coefficient is a matrix ($a_{ij}$ (i=1, 2, . . . , n; j=1, 2, . . . , n)) satisfying Expression (1)

$$\begin{bmatrix} a_{11} & a_{12} & a_{13} & a_{14} & \ldots & a_{1n} \\ a_{21} & a_{22} & a_{23} & a_{24} & \ldots & a_{2n} \\ a_{31} & a_{32} & a_{33} & a_{34} & \ldots & a_{3n} \\ a_{41} & a_{42} & a_{43} & a_{44} & \ldots & a_{4n} \\ \vdots & \vdots & \vdots & \vdots & \vdots & \vdots \\ a_{n1} & a_{n2} & a_{n3} & a_{n4} & \ldots & a_{nn} \end{bmatrix} \begin{bmatrix} Y_1 \\ Y_2 \\ Y_3 \\ Y_4 \\ \vdots \\ Y_n \end{bmatrix} = \begin{bmatrix} X_1 \\ X_2 \\ X_3 \\ X_4 \\ \vdots \\ X_n \end{bmatrix} \quad (1)$$

where the plurality of fluorescent coloring matters mixed in the sample are given numbers 1 to n, and when the light source unit irradiates the sample with light having an excitation wavelength of a k-th fluorescent coloring matter (k=1, 2, ..., n), an output value of the electrical signal output by the light receiving unit is represented by $X_k$, and a fluorescence intensity of the k-th fluorescent coloring matter is represented by $Y_k$. The calculation section substitutes the matrix ($a_{ij}$) and the output values $X_1$ to $X_n$ into Expression (1) to calculate the fluorescence intensities $Y_1$ to $Y_n$ as the fluorescence intensities of the fluorescent coloring matters.

Further, in the embodiment in which the measuring instrument functions as a fluorescence measuring instrument, preferably, the measuring instrument has a light amount monitor that detects a light amount of light emitted by the light source unit and outputs a signal to the calculation section. The calculation section corrects the output values $X_1$ to $X_n$ or the matrix elements $a_{11}$ to $a_{nn}$ based on the signal output by the light amount monitor.

Next, to achieve the above-described object, a fluorometric method of the present invention is a method for measuring a fluorescence intensity of fluorescence of each of a plurality of fluorescent coloring matters, the fluorescence being emitted from a sample mixed with the plurality of fluorescent coloring matters having different excitation wavelengths, by using a light source unit capable of emitting light having different wavelengths and a light receiving unit that receives the fluorescence of the fluorescent coloring matters and outputs an electrical signal corresponding to the fluorescence intensity of the received fluorescence. The method comprises calculating the fluorescence intensity of the fluorescence of each fluorescent coloring matter emitted from the sample using a correction coefficient. The correction coefficient is calculated based on an electrical signal output by the light receiving unit when the light source unit irradiates each of a plurality of correction samples, each correction sample being mixed with one of the plurality of fluorescent coloring matters and the respective mixed fluorescent coloring matters being different from one another, with light having a corresponding excitation wavelength of the plurality of fluorescent coloring matters.

In the fluorometric method of the present invention, preferably, the correction coefficient is a matrix ($a_{ij}$ (i=1, 2, ..., n; j=1, 2, ..., n)) satisfying Expression (1) where the plurality of fluorescent coloring matters mixed in the sample are given numbers 1 to n, and when the light source unit irradiates the sample with light having an excitation wavelength of a k-th fluorescent coloring matter (k=1, 2, ..., n), an output value of the electrical signal output by the light receiving unit is represented by $X_k$, and a fluorescence intensity of the k-th fluorescent coloring matter is represented by $Y_k$, and the matrix ($a_{ij}$) and the output values $X_1$ to $X_n$ are substituted into Expression (1) to calculate the fluorescence intensities $Y_1$ to $Y_n$ as the fluorescence intensities of the fluorescent coloring matters.

Further, in the fluorometric method of the present invention, preferably, the output values $X_1$ to $X_n$ or the matrix elements $a_{11}$ to $a_{nn}$ are corrected based on a light amount of light emitted by the light source unit.

Furthermore, the present invention may be a program that implements the fluorometric method of the present invention. By installing the program into a computer and executing the program, the fluorometric method of the present invention can be performed. Note that the term "coloring matter" as used herein includes a fluorescent coloring matter for use in fluorescence measurement in addition to coloring matters for use in absorbance measurement and reflectance measurement. When only a fluorescent coloring matter is specified among the "coloring matters", the term "fluorescent coloring matter" is used.

BEST MODE FOR CARRYING OUT THE INVENTION

Figure 1:
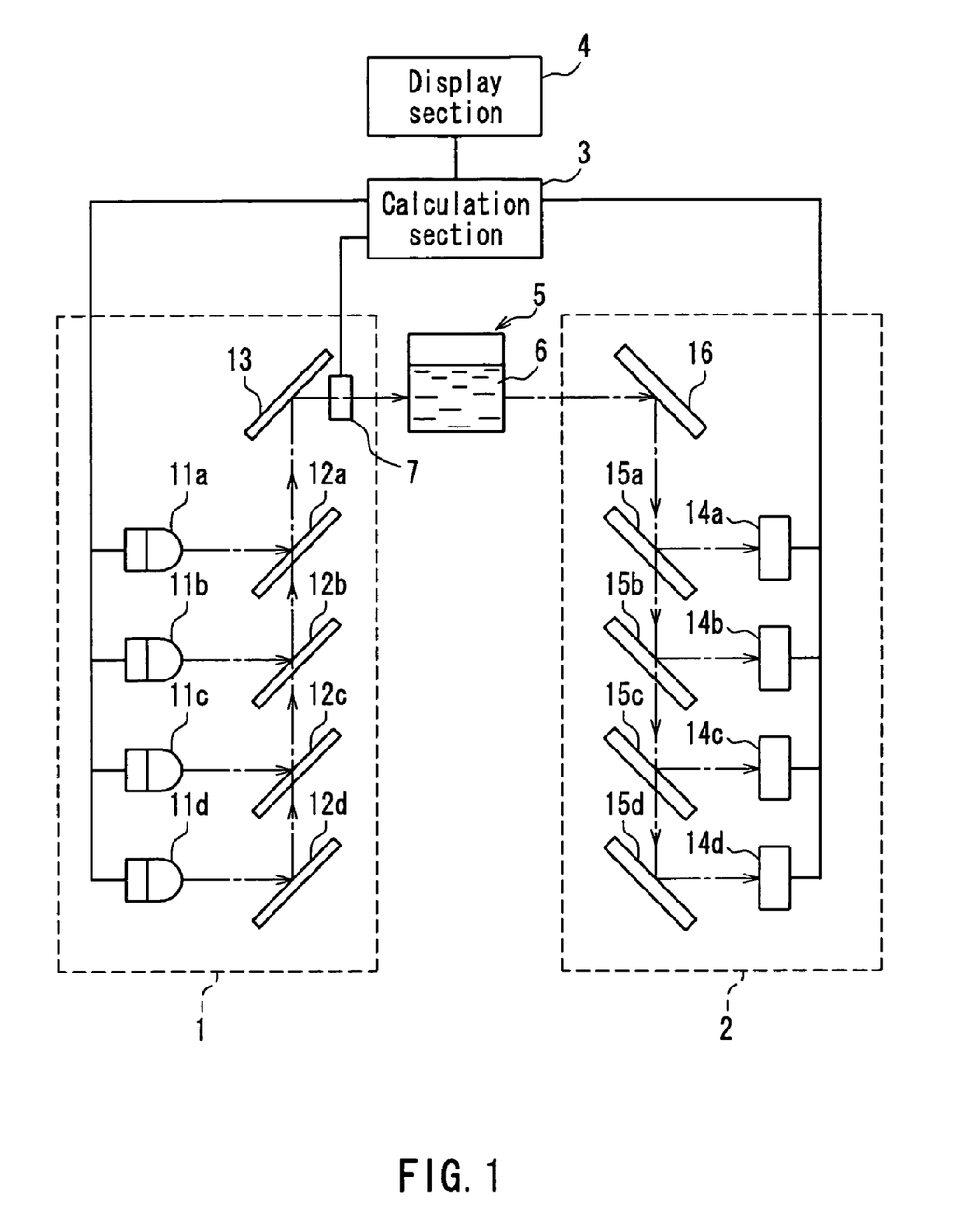
FIG. 1 is a structural diagram showing a fluorescence measuring instrument according to an embodiment of the measuring instrument of the present invention.

Hereinafter, an exemplary measuring instrument and fluorometric method of the present invention will be described with reference to the accompanying drawings. Note that, in the following description, the measuring instrument of the present invention is a fluorescence measuring instrument, for example. Firstly, a structure of a fluorescence measuring instrument according to an embodiment of the measuring instrument of the present invention will be described with reference to FIG. 1. FIG. 1 is a structural diagram showing the fluorescence measuring instrument according to an embodiment of the measuring instrument of the present invention.

The fluorescence measuring instrument of FIG. 1 is an instrument for measuring a fluorescence intensity of fluorescence emitted from each fluorescent coloring matter in a sample 6. As shown in FIG. 1, the fluorescence measuring instrument comprises a light source unit 1, a light receiving unit 2, a calculation section 3, a display section 4, a reaction vessel 5, and a light amount monitor 7.

The sample 6 mixed with a plurality of fluorescent coloring matters is placed in the reaction vessel 5. In the example of FIG. 1, the sample is mixed with four fluorescent coloring matters shown in Table 1 below. Note that, in the present invention, the fluorescent coloring matters mixed into a sample are not limited to those shown in Table 1 below and the number of the fluorescent coloring matters also is not limited. In the present invention, a required number of appropriate fluorescent coloring matters can be selected, depending on the purpose the fluorescence measurement or the like.

TABLE 1

| Name of fluorescent coloring matter | FAM | JOE | TAMRA | ROX |
|---|---|---|---|---|
| Excitation peak wavelength [nm] | 470 | 500 | 530 | 560 |
| Fluorescence peak wavelength [nm] | 520 | 550 | 580 | 610 |

The light source unit 1 has a structure capable of emitting light having different wavelengths and can irradiate a sample with light having excitation wavelengths of fluorescent coloring matters mixed in the sample. In the example of FIG. 1, the light source unit 1 comprises light emitting devices 11a to 11d, dichroic mirrors 12a to 12d, and a total reflection mirror 13.

The light emitting devices 11a to 11d emit light in response to an instruction of the calculation section 3. The light is used to excite the fluorescent coloring matters mixed in the sample 6. The light emitting devices 11a to 11d are disposed in a manner that causes light beams emitted by the light emitting devices to be directed in parallel to one another. The light emitting devices 11a to 11d emit light having wavelengths different from one another. The individual wavelengths are set to be the excitation wavelength of one of the fluorescent coloring matters mixed in the sample. Specifically, the light emitting device 11a emits light having the excitation wavelength of FAM, the light emitting device 11b emits light having the excitation wavelength of JOE, the light emitting device 11c emits light having the excitation wavelength of TAMRA, and the light emitting device 11d emits light having the excitation wavelength of ROX.

The dichroic mirrors 12a to 12d have (high-pass) characteristics that allow only light having a specific wavelength or less to be reflected. The maximum wavelength of light that can be reflected by the dichroic mirror is increased in the order: 12a, 12b, 12c, 12d.

Therefore, light emitted from each of the light emitting devices 11a to 11d travels on the same optical path to enter the total reflection mirror 13, and is reflected from the total reflection mirror 13 to enter the reaction vessel 5. An amount of light emitted from the light emitting devices 11a to 11d is monitored by the light amount monitor 7. The light amount monitor 7 detects the amount of light emitted by the light emitting devices 11a to 11d and outputs a signal to the calculation section 3.

Note that, in the example of FIG. 1, since the number of fluorescent coloring matters used is four, the number of light emitting devices constituting the light source unit 1 is also four. The number of dichroic mirrors is also four, corresponding to the number of light emitting devices. Note that, in the present invention, the number of light emitting devices and the number of dichroic mirrors are not limited to this, and are determined depending on the number of fluorescent coloring matters used. As the light emitting devices 11a to 11d, light emitting diodes or semiconductor lasers are used preferably, and xenon lamps or halogen lamps also can be used.

The light receiving unit 2 receives fluorescence emitted from the reaction vessel 5, and outputs an electrical signal corresponding to a fluorescence intensity of the received fluorescence. In the example of FIG. 1, the light receiving unit comprises light receiving devices 14a to 14d, dichroic mirrors 15a to 15d, and a total reflection mirror 16.

In the example of FIG. 1, the dichroic mirrors 15a to 15d have (low-pass) characteristics that allow light having a specific wavelength or more to be reflected. The minimum wavelength of light that can be reflected by the dichroic mirror is increased in the order: 15d, 15c, 15b, 15a. The light receiving devices 14a to 14d are photodiodes and are arranged in a manner such that light reflected from one dichroic mirror enters the light receiving surface (not shown) of one light receiving device.

Therefore, fluorescence emitted from the reaction vessel 5 is reflected from the total reflection mirror 16, and thereafter is reflected from one of the dichroic mirrors 15a to 15d, depending on the wavelength of the fluorescence to enter a corresponding light receiving device. As a result, each light receiving device outputs an electrical signal corresponding to a fluorescence intensity of fluorescence to the calculation section 3.

The calculation section 3 calculates fluorescence intensity based on the electrical signal output from the light receiving unit 2. A result of the calculation is displayed on the display section 4. The display section 4 is a liquid crystal display apparatus, a CRT or the like.

Next, a fluorometric method of the present invention will be described with reference to FIGS. 2 to 4. Note that the fluorometric method of the present invention can be performed by operating the fluorescence measuring instrument of FIG. 1. Therefore, in the following description, an operation of the fluorescence measuring instrument of FIG. 1 will be described.

Figure 2:
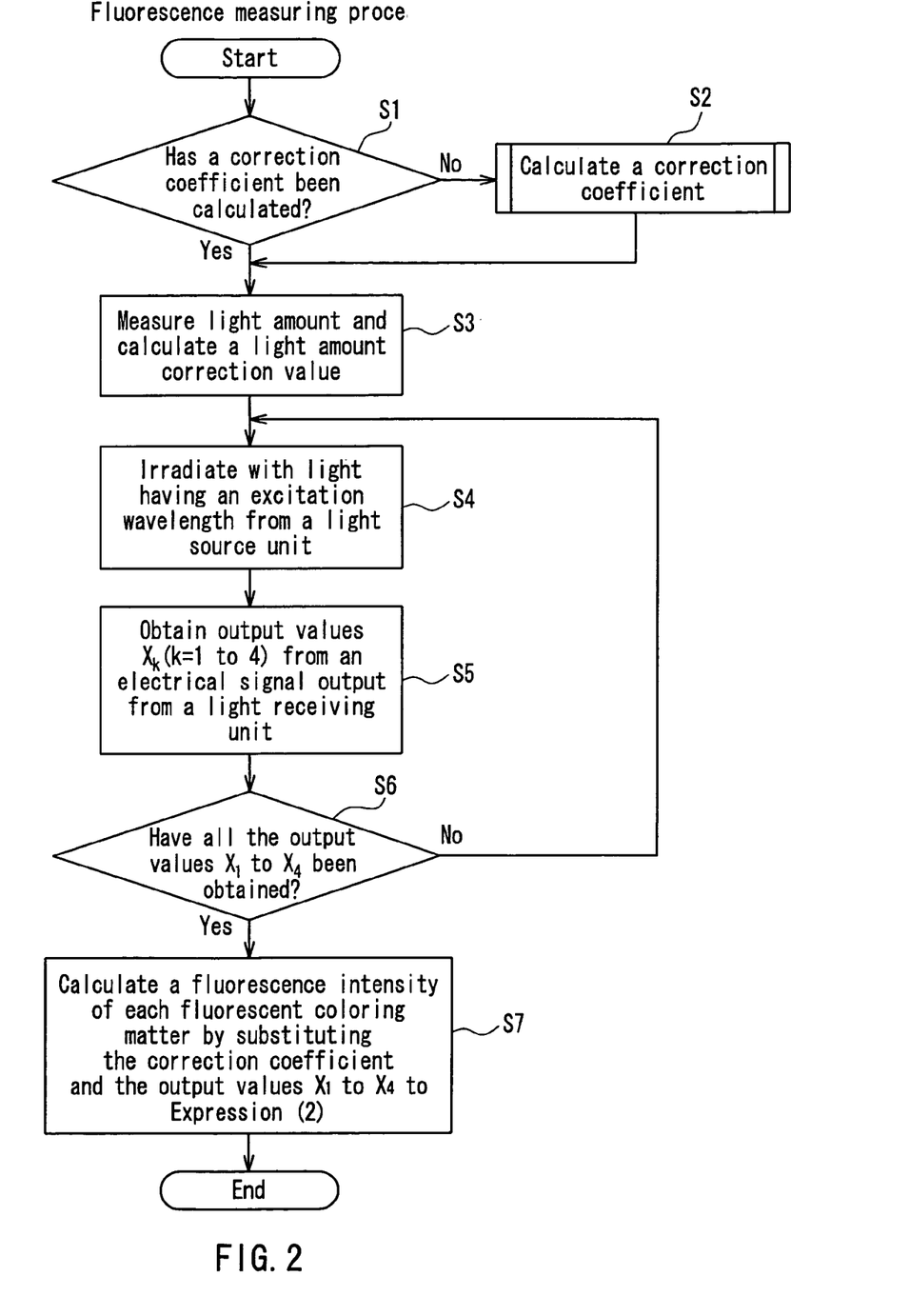
FIG. 2 is a flowchart showing a fluorescence measurement process performed by a fluorescence measuring instrument of FIG. 1.

FIG. 2 is a flowchart showing a fluorescence measurement process performed by the fluorescence measuring instrument of FIG. 1. As shown in FIG. 2, the calculation section 3 of the fluorescence measuring instrument initially determines whether or not a correction coefficient has been calculated (step S1). The correction coefficient is used for calculation of fluorescence intensity for each fluorescent coloring matter based on an electrical signal output by the light receiving unit 2 when a sample mixed with a plurality of fluorescent coloring matters is irradiated with light having an excitation wavelength of each fluorescent coloring matter.

As used herein, the term "fluorescence intensity of each fluorescent coloring matter" refers to, not a combined value obtained in conventional fluorescence measurement, but an intensity of fluorescence emitted only by a fluorescent coloring matter whose excitation wavelength corresponds to the wavelength of the light when a sample is irradiated with light. In the present invention, the above-described correction coefficient is used to separate an actual fluorescence intensity from a combined value as described below.

In the example of FIG. 2, the correction coefficient is a matrix $(a_{ij})$ that satisfies the above-described expression (1). Note that, in the example, the number of fluorescent coloring matters mixed in a sample is four as described above. Therefore, the four fluorescent coloring matters mixed in a sample are given numbers 1 to 4 in order of excitation wavelength from the shortest. The correction coefficient is a matrix ($a_{ij}$ (i=1, 2, 3, 4; j=1, 2, 3, 4)) that satisfies Expression (2) below:

$$\begin{bmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{bmatrix} \begin{bmatrix} Y_1 \\ Y_2 \\ Y_3 \\ Y_4 \end{bmatrix} = \begin{bmatrix} X_1 \\ X_2 \\ X_3 \\ X_4 \end{bmatrix} \quad (2)$$

where, when the light source unit 1 irradiates a sample with light having the excitation wavelength of a k-th fluorescent coloring matter (k=1, 2, 3, 4), an output value of an electrical signal output by the light receiving unit 2 is represented by $X_k$, and the fluorescence intensity of the k-th fluorescent coloring matter is represented by $Y_k$.

When it is determined in step S1 that the correction coefficient has not yet been calculated, the calculation section 3 performs a correction coefficient calculation process (step S2), and thereafter, step S3 below. Note that the correction coefficient calculation process of step S2 specifically will be described below.

On the other hand, when it is determined that the correction coefficient has been calculated in step S1, the calculation section 3 causes each of the light emitting devices 11$a$ to 11$d$ to emit light and causes the light amount monitor 7 to measure the amount of light. When the measured light amount is varied, the calculation section 3 calculates a light amount correction value for correcting output values $X_1$ to $X_4$ described below (step S3). Note that details of step S3 will be described below.

Next, the calculation section 3 causes each light emitting device of the light source unit 1 to emit light having an excitation wavelength toward a sample in order to measure fluorescence intensity (step S4). Thereafter, the calculation section 3 receives an electrical signal output by the light receiving unit 2 to obtain its output value $X_k$ (k=1 to 4) (step S5).

Note that, in the example of FIGS. 1 to 4, the output value of the electrical signal output by the light receiving unit 2 is a digital value that is obtained by I/V converting a current value of an electrical signal output by the light receiving devices 14$a$ to 14$d$ and further A/D converting the resultant voltage value. However, the present invention is not limited to this. The output value of the electrical signal output by the light receiving unit 2 may be a digital value obtained by A/D converting the current value of the electrical signal output by the light receiving devices 14$a$ to 14$d$.

Thereafter, the calculation section 3 determines whether or not all the output values $X_1$ to $X_4$ have been obtained (step S6). When not all the output values $X_1$ to $X_4$ have been obtained, the calculation section 3 performs steps S4 and S5 again.

On the other hand, when all the output values $X_1$ to $X_4$ have been obtained, the calculation section 3 substitutes the correction coefficient and the output values $X_1$ to $X_4$ obtained in step S5 into the above-described Expression (2) to calculate fluorescence intensities $Y_1$ to $Y_4$ of the fluorescent coloring matters (step S7). Note that, when a light amount correction value has been calculated in step S3, the output values $X_1$ to $X_4$ or the matrix elements of the matrix ($a_{ij}$ (i=1, 2, 3, 4; j=1, 2, 3, 4)) corrected using the light amount correction value are substituted into Expression (2).

The above-described fluorescence measurement process is then ended, and the fluorescence intensity of each fluorescent coloring matter is displayed on the display section 4. Thus, the fluorescence measuring instrument and the fluorometric method of the present invention can be used to separate actual fluorescence intensity from a combined value, resulting in more accurate fluorescence measurement than conventional techniques.

Next, the correction coefficient calculation process in step S2 of FIG. 2 will be described with reference to FIG. 3. FIG. 3 is a flowchart showing the correction coefficient calculation process performed in the fluorescence measuring instrument of FIG. 1.

The correction coefficient calculation process is performed using a plurality of samples for correction. Each correction sample is mixed with only one of the fluorescent coloring matters to be mixed in a sample. The fluorescent coloring matters mixed in the respective correction samples are different from one another. Specifically, in the example of FIG. 3, a sample is mixed with four fluorescent coloring matters as shown in Table 1, and therefore, four correction samples are required.

The correction coefficient calculation process is performed using Expressions (3) to (6) below, which are obtained by expanding Expression (2).

$$a_{11}Y_1 + a_{12}Y_2 + a_{13}Y_3 + a_{14}Y_4 = X_1 \quad (3)$$

$$a_{21}Y_1 + a_{22}Y_2 + a_{23}Y_3 + a_{24}Y_4 = X_2 \quad (4)$$

$$a_{31}Y_1 + a_{32}Y_2 + a_{33}Y_3 + a_{34}Y_4 = X_3 \quad (5)$$

$$a_{41}Y_1 + a_{42}Y_2 + a_{43}Y_3 + a_{44}Y_4 = X_4 \quad (6)$$

Figure 3:
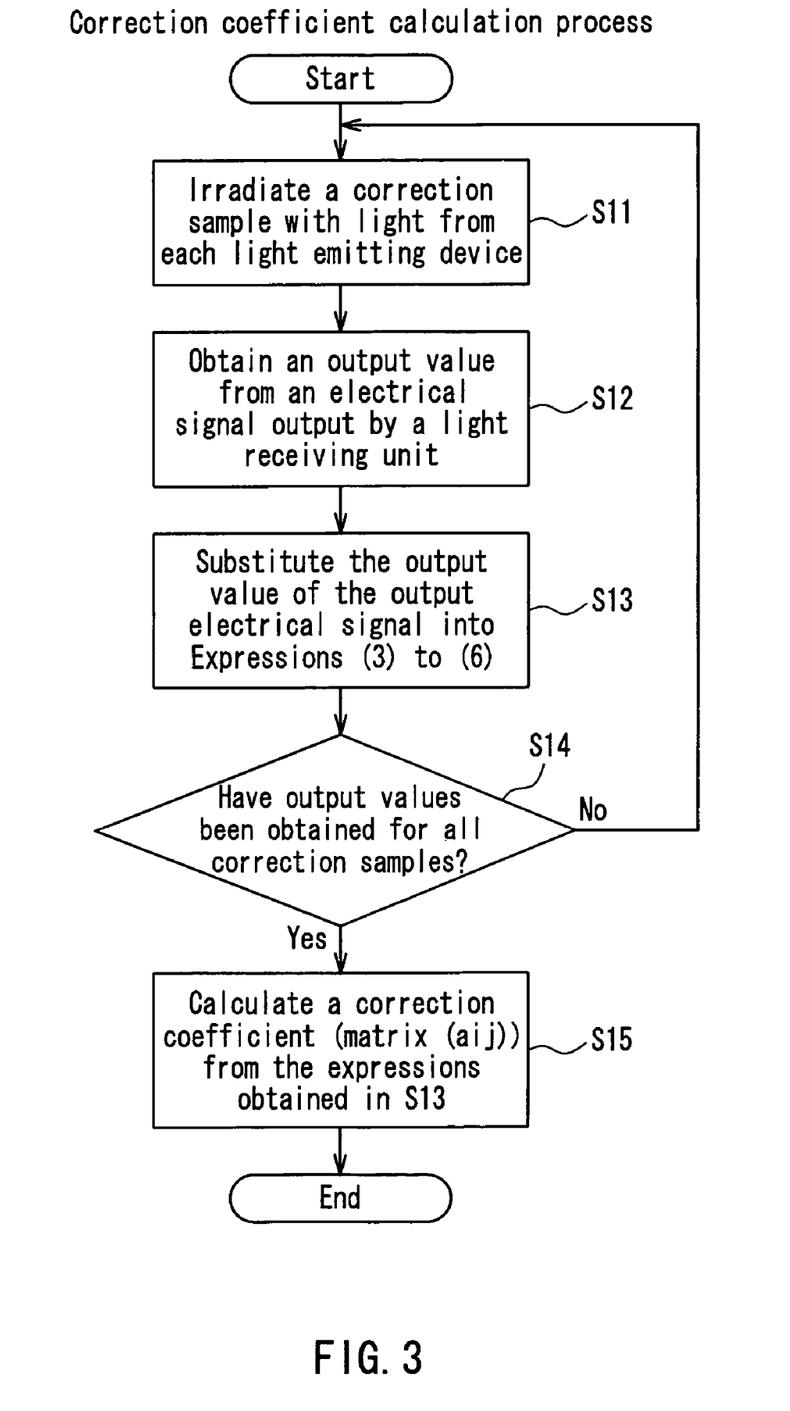
FIG. 3 is a flowchart showing a correction coefficient calculation process performed in the fluorescence measuring instrument of FIG. 1.

As shown in FIG. 3, the calculation section 3 initially irradiates the correction sample with light from each light emitting device (step S11), and then obtains an output value of an electrical signal output by the light receiving unit 2 (step S12). Thereafter, the calculation section 3 substitutes the obtained output values into Expressions (3) to (6) (step S13).

Next, the calculation section 3 determines whether or not output values have been obtained from all the correction samples (step S14). When output values have been obtained from not all the correction samples, steps S11 to S13 are performed again. When output values have been obtained from all the correction samples, step S15 is performed.

Steps S11 to S13 will be described specifically. The calculation section 3 initially irradiates a correction sample mixed only with a first fluorescent coloring matter (FAM), with light having the excitation wavelengths of first to fourth fluorescent coloring matters using the light source unit 1. In this case, output values of output electrical signals are represented by F1 to F4, corresponding to the names of the fluorescent coloring matters. The calculation section 3 substitutes the output values F1 to F4 into $X_1$ to $X_4$ of Expressions (3) to (6). Also in this case, since the correction sample is mixed only with the first fluorescent coloring matter, $Y_2 = Y_3 = Y_4 = 0$ (zero) in Expressions (3) to (6). Therefore, Expressions (7) to (10) below are obtained.

$$a_{11}Y_1 = F1 \quad (7)$$

$$a_{21}Y_1 = F2 \quad (8)$$

$$a_{31}Y_1 = F3 \quad (9)$$

$$a_{41}Y_1 = F4 \quad (10)$$

Similarly, the calculation section 3 irradiates a correction sample mixed only with a second fluorescent coloring matter (JOE), a correction sample mixed with a third fluorescent coloring matter (TAMRA), and a correction sample mixed only with a fourth fluorescent coloring matter (ROX), with light having the excitation wavelengths of the first to fourth fluorescent coloring matters using the light source unit 1, obtains output values of output electrical signals, and substitutes the obtained output values into Expressions (3) to (6). The output values in these cases are represented by J1 to J4, T1 to T4, and R1 to R4, respectively. In this case, Expressions (11) to (22) below are obtained.

$$a_{12}Y_2 = J1 \tag{11}$$

$$a_{22}Y_2 = J2 \tag{12}$$

$$a_{32}Y_2 = J3 \tag{13}$$

$$a_{42}Y_2 = J4 \tag{14}$$

$$a_{13}Y_3 = T1 \tag{15}$$

$$a_{23}Y_3 = T2 \tag{16}$$

$$a_{33}Y_3 = T3 \tag{17}$$

$$a_{43}Y_3 = T4 \tag{18}$$

$$a_{14}Y_4 = R1 \tag{19}$$

$$a_{24}Y_4 = R2 \tag{20}$$

$$a_{34}Y_4 = R3 \tag{21}$$

$$a_{44}Y_4 = R4 \tag{22}$$

Next, in step S15, the calculation section 3 uses Expressions (7) to (22) obtained in step S13 to calculate a matrix ($a_{ij}$ (i=1, 2, 3, 4; j=1, 2, 3, 4)) that satisfies Expression (2), as a correction coefficient.

Specifically, the calculation section 3 sets $a_{11}=a_{22}=a_{33}=a_{44}=1$ to calculate the correction coefficient. For example, a ratio of $a_{11}:a_{12}:a_{13}:a_{14}$ is determined, depending on a fluorescent coloring matter used. Therefore, the calculation section 3 calculates $a_{12}$=J1/F1, $a_{13}$=T1/F1, and $a_{14}$=R1/F1.

Similarly, the calculation section 3 calculates $a_{21}$=F2/J2, $a_{23}$=T2/J2, and $a_{24}$=R2/J2. The calculation section 3 also calculates $a_{31}$=F3/T3, $a_{32}$=J3/T3, and $a_{34}$=R3/T3. Further, the calculation section calculates $a_{41}$=F4/R4, $a_{42}$=J4/R4, and $a_{43}$=T4/R4.

The above-described correction coefficient calculation process is then ended. Note that the correction coefficient calculation process can be performed before shipment of the fluorescence measuring instrument of the present invention. In this case, it is preferable that the correction coefficient previously is stored in a memory in the fluorescence measuring instrument before product shipment. Also in this case, steps S1 and S2 do not have to be performed in the fluorescence measurement process of FIG. 2.

Next, correction of an output value based on a light amount, which is shown in step S3 of FIG. 2, will be described with reference to FIG. 4. FIG. 4 is a flowchart showing a light amount correction value calculation process performed in the fluorescence measuring instrument of FIG. 1.

When the light amounts of the light emitting devices 11a to 11d vary with time and environment, the ratio of $a_{11}:a_{21}:a_{31}:a_{41}$, the ratio of $a_{12}:a_{22}:a_{32}:a_{42}$, the ratio of $a_{13}:a_{23}:a_{33}:a_{43}$, and the ratio of $a_{14}:a_{24}:a_{34}:a_{44}$ are influenced, so that it is no longer possible to calculate a fluorescence brightness accurately. To prevent this, the light amount correction value calculation process of FIG. 4 is performed.

Figure 4:
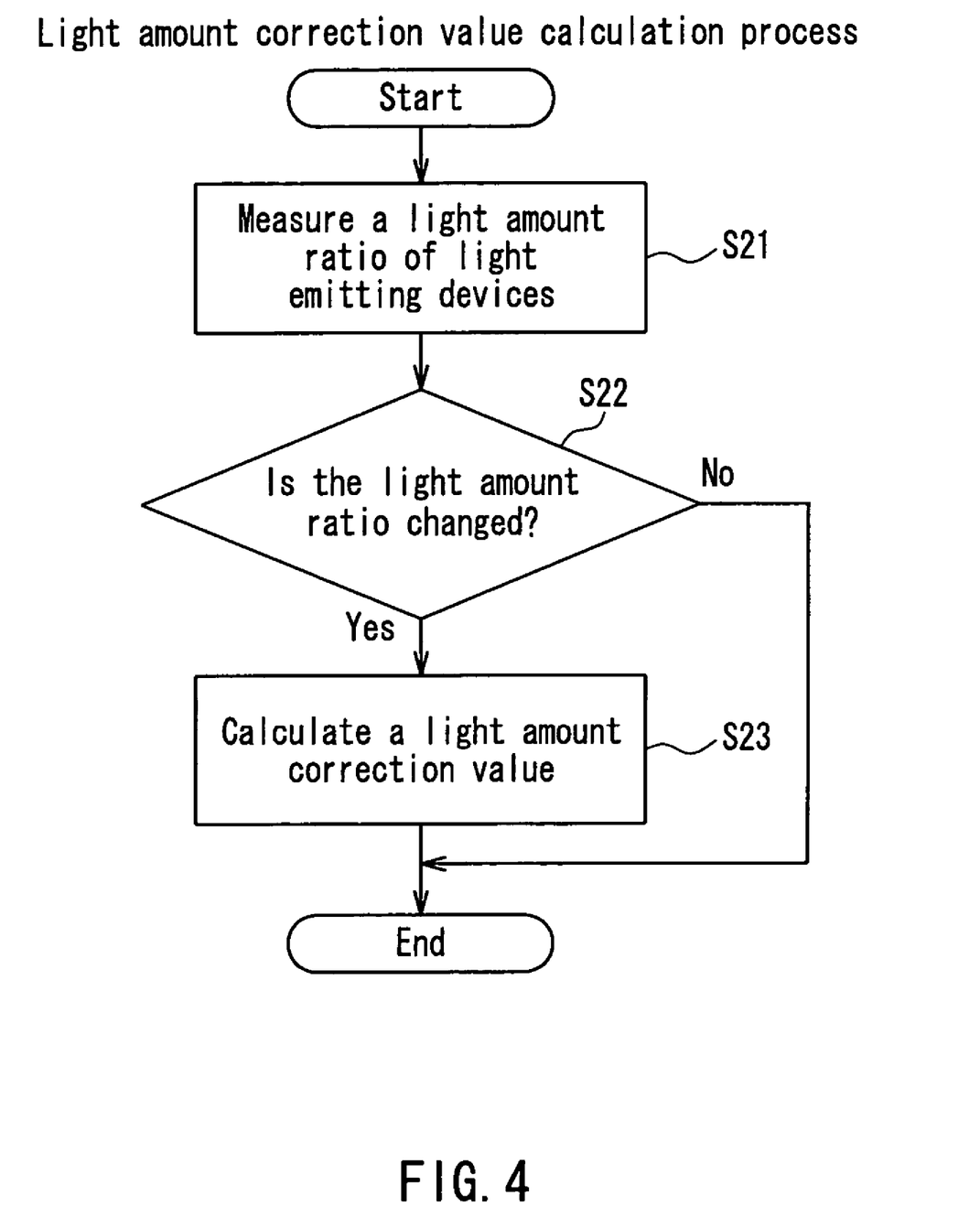
FIG. 4 is a flowchart showing a light amount correction value calculation process performed in the fluorescence measuring instrument of FIG. 1.

Specifically, as shown in FIG. 4, the calculation section 3 initially measures a current light amount ratio of the light emitting devices 11a, 11b, 11c and 11d based on a signal from a light amount monitor where the light amount ratio of the light emitting devices when the correction coefficient was determined is assumed to be 1:1:1:1 (reference value) (step S21).

Next, the calculation section 3 determines whether or not the obtained light amount ratio is changed from 1:1:1:1 (step S22). When the light amount ratio is not changed, the calculation section 3 ends the process. On the other hand, when the light amount ratio is changed, the calculation section 3 calculates a light amount correction value corresponding to a change width (step S23).

For example, it is assumed that the ratio of light amounts of the light emitting devices 11a, 11b, 11c and 11d is 1:2:3:4. In this case, in order to return the light amount ratio to a reference value, the light amount of each light emitting device needs to be multiplied by 1/1, 1/2, 1/3, or 1/4. Therefore, the light amount correction values are 1/1, 1/2, 1/3, and 1/4. Note that, when the light receiving devices 14a to 14d have a low level of sensitivity, a variation in light amount has a small influence on fluorescence intensity. When the sensitivity is high, the reverse is true. Therefore, it can be said that the light amount correction value preferably is determined, taking into consideration the sensitivities of the light receiving devices 14a to 14d.

Therefore, the calculation section 3 substitutes $(1/1)X_1$, $(1/2)X_2$, $(1/3)X_3$ and $(1/4)X_4$ instead of $X_1$, $X_2$, $X_3$ and $X_4$ into Expression (2) to calculates the fluorescence intensities $Y_1$ to $Y_4$ in step S7 of FIG. 2. Alternatively, the calculation section 3 substitutes $(1/1)a_{i1}$, $(1/2)a_{i2}$, $(1/3)a_{i3}$, and $(1/4)a_{i4}$ instead of matrix elements $a_{i1}$, $a_{i2}$, $a_{i3}$, and $a_{i4}$ into the matrix ($a_{ij}$(i=1, 2, 3, 4; j=1, 2, 3, 4)) that satisfies Expression (2) to calculate the fluorescence intensity $Y_1$ to $Y_4$.

Thus, according to the fluorescence measuring instrument and the fluorometric method of FIG. 1, even if the light amounts of light emitting devices vary, fluorescence intensity can be calculated based on corrected light amounts of the light emitting devices, thereby making it possible to improve the accuracy of fluorescence measurement further.

Note that the fluorescence measuring instrument of FIG. 1 can be implemented by installing a program that causes a computer connected to the light source unit 1 and the light receiving unit 2 to execute steps S1 to S7 of FIG. 2 and performing the program. In this case, the CPU (central processing unit) of the computer functions as the calculation section 3.

In the above-described embodiments, the fluorescence measuring instrument and the fluorometric method are described as examples. Note that the present invention is not limited to the examples. The present invention may be applied to a measuring instrument or method using absorbance or reflectance measurement. Specifically, according to the present invention, even when a sample is mixed with a plurality of coloring matters having different absorption wavelengths or reflection wavelengths, a correction coefficient can be calculated in the same manner as described above and the intensity of transmitted light or scattered light can be calculated for each coloring matter. Further, an absorbance can be calculated based on the calculated intensity of transmitted light, and a reflectance can be calculated based on the intensity of scattered light.

INDUSTRIAL APPLICABILITY

As described above, according to the measuring instrument and the fluorometric method of the present invention, even when a sample is mixed with a plurality of coloring matters (e.g., fluorescent coloring matters), the actual intensity of each coloring matter can be separated from the resultant (fluorescence) intensity of transmitted light or radiated light. Therefore, by using the measuring instrument and the fluorometric method of the present invention, it is possible to perform more accurate component analysis, genetic diagnosis and the like than with conventional techniques.

The invention claimed is:

1. A measuring instrument for measuring fluorescence intensity of fluorescence of each of a plurality of fluorescent coloring matters when a sample mixed with the plurality of fluorescent coloring matters having different excitation wavelengths and having numbers 1 to n given thereto is irradiated with light having different wavelengths, comprising:
a light source unit capable of irradiating the sample with the light having the different wavelengths; a light receiving unit that receives fluorescence of the fluorescent coloring matters and outputs an electrical signal corresponding to a fluorescence intensity of the received fluorescence; a calculation section and a light amount monitor that detects a light amount of light emitted by the light source unit and outputs a signal to the calculation section,
wherein the calculation section calculates the fluorescence intensity of the fluorescence of each of the fluorescent coloring matters emitted from the sample using a correction coefficient that is calculated based upon an output value $X_k$ of the electrical signal output by the light receiving unit when the light source unit irradiates each of a plurality of correction samples, each correction sample being mixed with one of the plurality of fluorescent coloring matters and the respective mixed fluorescent coloring matters being different from one another, with light having an excitation wavelength of a k-th fluorescent coloring matter (k=1, 2, . . . , n),
assuming that a fluorescent intensity of the k-th fluorescent coloring matter is represented by $Y_k$ in the sample mixed with the plurality of fluorescent coloring matters, the correction coefficient is a matrix ($a_{ij}$ (i=1, 2, . . . , n; j=1, 2, . . . , n)) satisfying Expression (23):

$$\begin{bmatrix} a_{11} & a_{12} & a_{13} & a_{14} & \ldots & a_{1n} \\ a_{21} & a_{22} & a_{23} & a_{24} & \ldots & a_{2n} \\ a_{31} & a_{32} & a_{33} & a_{34} & \ldots & a_{3n} \\ a_{41} & a_{42} & a_{43} & a_{44} & \ldots & a_{4n} \\ \vdots & \vdots & \vdots & \vdots & \vdots & \vdots \\ a_{n1} & a_{n2} & a_{n3} & a_{n4} & \ldots & a_{nn} \end{bmatrix} \begin{bmatrix} Y_1 \\ Y_2 \\ Y_3 \\ Y_4 \\ \vdots \\ Y_n \end{bmatrix} = \begin{bmatrix} X_1 \\ X_2 \\ X_3 \\ X_4 \\ \vdots \\ X_n \end{bmatrix} \quad (23)$$

wherein the calculation section corrects the output values $X_1$ to $X_n$ or the matrix elements $a_{11}$ to $a_{nn}$ based on the signal output by the light amount monitor.

2. A fluorometric method for measuring a fluorescence intensity of fluorescence of each of a plurality of fluorescent coloring matters, the fluorescence being emitted from a sample mixed with the plurality of fluorescent coloring matters having different excitation wavelengths and having numbers 1 to a given thereto, by using a light source unit capable of emitting light having different wavelengths and a light receiving unit that receives the fluorescence of the fluorescent coloring matters and outputs an electrical signal corresponding to the fluorescence intensity of the received fluorescence, the method comprising:
calculating the fluorescence intensity of the fluorescence of each fluorescent coloring matter emitted from the sample using a correction coefficient,
wherein the correction coefficient is calculated based on an output value $X_k$ of the electrical signal output by the light receiving unit when the light source unit irradiates each of a plurality of correction samples, each correction sample being mixed with one of the plurality of fluorescent coloring matters and the respective mixed fluorescent coloring matters being different from one another, with light having an excitation wavelength of a k-th fluorescent coloring matter (k=1, 2, . . . , n), and assuming that a fluorescence intensity of the k-th fluorescent coloring matter is represented by $Y_k$ in the sample mixed with the plurality of fluorescent coloring matters, the correction coefficient is a matrix ($a_{ij}$ (i=1, 2, . . . , n; j=1, 2, . . . , n)) satisfying Expression (24):

$$\begin{bmatrix} a_{11} & a_{12} & a_{13} & a_{14} & \ldots & a_{1n} \\ a_{21} & a_{22} & a_{23} & a_{24} & \ldots & a_{2n} \\ a_{31} & a_{32} & a_{33} & a_{34} & \ldots & a_{3n} \\ a_{41} & a_{42} & a_{43} & a_{44} & \ldots & a_{4n} \\ \vdots & \vdots & \vdots & \vdots & \vdots & \vdots \\ a_{n1} & a_{n2} & a_{n3} & a_{n4} & \ldots & a_{nn} \end{bmatrix} \begin{bmatrix} Y_1 \\ Y_2 \\ Y_3 \\ Y_4 \\ \vdots \\ Y_n \end{bmatrix} = \begin{bmatrix} X_1 \\ X_2 \\ X_3 \\ X_4 \\ \vdots \\ X_n \end{bmatrix} \quad (24)$$

wherein in the calculating step, the output values $X_1$ to $X_n$ or the matrix elements $a_{11}$ to $a_{nn}$ are corrected based on a light amount of light emitted by the light source unit.

3. A computer program product comprising a program recorded in a recording medium, the program causing a computer to measure a fluorescence intensity of fluorescence of each of a plurality of fluorescent coloring matters, the fluorescence being emitted from a sample mixed with the plurality of fluorescent coloring matters having different excitation wavelengths and having numbers 1 to n given thereto, using a light source unit capable of emitting light having different wavelengths and a light receiving unit that receives the fluorescence of the fluorescent coloring matters and outputs an electrical signal corresponding to the fluorescence intensity of the received fluorescence, the program comprising,
the step of calculating the fluorescence intensity of the fluorescence of each fluorescent coloring matter emitted from the sample using a correction coefficient,
wherein the correction coefficient is calculated based on an output value $X_k$ of the electrical signal output by the light receiving unit when the light source unit irradiates each of a plurality of correction samples, each correction sample being mixed with one of the plurality of fluorescent coloring matters and the respective mixed fluorescent coloring matters being different from one another, with light having an excitation wavelength of a k-th fluorescent coloring matter (k=1, 2, . . . , n) and assuming that a fluorescence intensity of the k-th fluorescent coloring matter is represented by $Y_k$ in the sample mixed with the plurality of fluorescent coloring matters, the correction coefficient is a matrix ($a_{ij}$ (i=1, 2, . . . , n; j=1, 2, . . . , n)) satisfying Expression (25):

$$\begin{bmatrix} a_{11} & a_{12} & a_{13} & a_{14} & \ldots & a_{1n} \\ a_{21} & a_{22} & a_{23} & a_{24} & \ldots & a_{2n} \\ a_{31} & a_{32} & a_{33} & a_{34} & \ldots & a_{3n} \\ a_{41} & a_{42} & a_{43} & a_{44} & \ldots & a_{4n} \\ \vdots & \vdots & \vdots & \vdots & \vdots & \vdots \\ a_{n1} & a_{n2} & a_{n3} & a_{n4} & \ldots & a_{nn} \end{bmatrix} \begin{bmatrix} Y_1 \\ Y_2 \\ Y_3 \\ Y_4 \\ \vdots \\ Y_n \end{bmatrix} = \begin{bmatrix} X_1 \\ X_2 \\ X_3 \\ X_4 \\ \vdots \\ X_n \end{bmatrix} \quad (25)$$

wherein in the calculating step, the output values $X_1$ to $X_n$ or the matrix elements $a_{11}$ to $a_{nn}$ are corrected based on a light amount of light emitted by the light source unit.

\* \* \* \* \*